(12) United States Patent
Lee

(10) Patent No.: US 9,119,768 B1
(45) Date of Patent: Sep. 1, 2015

(54) DRY TYPE HALF BATH APPARATUS WITH FEET MASSAGE FUNCTION

(71) Applicant: Sang Won Lee, Yorba Linda, CA (US)

(72) Inventor: Sang Won Lee, Yorba Linda, CA (US)

( * ) Notice: Subject to any disclaimer, the term of this patent is extended or adjusted under 35 U.S.C. 154(b) by 0 days.

(21) Appl. No.: 14/591,862

(22) Filed: Jan. 7, 2015

(51) Int. Cl.
*A61H 33/06* (2006.01)
*A61H 15/00* (2006.01)

(52) U.S. Cl.
CPC .............. *A61H 33/067* (2013.01); *A61H 15/00* (2013.01); *A61H 33/063* (2013.01); *A61H 2201/0228* (2013.01)

(58) Field of Classification Search
CPC ... A61H 33/06; A61H 33/063; A61H 33/066; A61H 33/067

USPC ....................................... 4/524, 528, 530–532
See application file for complete search history.

(56) References Cited

U.S. PATENT DOCUMENTS

2003/0156831 A1* 8/2003 Schaeffer et al. .................. 4/524

* cited by examiner

*Primary Examiner* — Tuan N Nguyen
(74) *Attorney, Agent, or Firm* — John K. Park; Park Law Firm

(57) ABSTRACT

A dry type half bath apparatus with feet massage function is provided, which includes a main body comprising a door that opens and closes for a user's entering and leaving; a chair disposed in a rear inner portion of the main body for the user's sitting thereon; at least one far-infrared generator disposed in the main body and illuminating far-infrared to skin of the user sitting on the chair; and a feet massaging device disposed in a front inner portion of the main body for receiving the user's feet and massaging sole, top, and ankle of the feet.

20 Claims, 3 Drawing Sheets

DRY TYPE HALF BATH APPARATUS WITH FEET MASSAGE FUNCTION

FIELD OF TECHNOLOGY

The present invention relates to a dry type half bath apparatus with feet massage function, and more specifically to a dry type half bath apparatus with feet massage function, which can be used for feet massage while half bath.

BACKGROUND OF THE INVENTION

In general, half bath is a method of bath for cooling head portion and warming feet by warming the lower half body, getting rid of coldness in lower body that causes problems in blood circulation.

With the half bath, it can be expected that the blood vessels are expanded lowering blood pressure, recovery from fatigue and metabolism are facilitated, and toxin accumulated in the body are discarded through perspiration. As people get interested in half bath with such merits, more and more half bath devices have been introduced recently, and many half bath devices with various functions have been developed.

Such half bath devices are categorized into wet type and dry type of half bath devices. The wet type half bath device is for filling up water within and heating water for bathing the lower half body, but the efficiency is very compromised since it is not environment-friendly, it takes a lot of electrical power to heat up water and maintain, and it is very cumbersome to exchange water. The dry type half bath device is for bathing using surface-type heating body emitting far-infrared or a far-infrared lamp, and has been used since it can solve problems of the wet type 0 hf device.

One of such dry type 0 hf devices was described in a registered Korean Patent No. 0410450. The 0 hf device disclosed in the Korean patent provides various functions such as humidifying function for preventing skin problem, sole-massaging function, and fat-removing function through imparting vibration to waist or thigh portions in addition to the half bath function.

However, in the half bath device of the above patent, since the feet massaging device installed in the half bath device includes roller-type only, there were problems that massage was possible just to the sole and the users must contact and press down their feet on the feet massaging device.

SUMMARY OF THE INVENTION

Problem to Solve

The present invention contrives to solve the disadvantages of the prior art, and provides a dry type half bath apparatus with feet massage function enabling feet massage during half bath.

Solutions to Problem

In order to achieve the above purposes, a dry type half bath apparatus with feet massage function according to the invention includes a main body comprising a door that opens and closes for a user's entering and leaving; a chair disposed in a rear inner portion of the main body for the user's sitting thereon; at least one far-infrared generator disposed in the main body and illuminating far-infrared to skin of the user sitting on the chair; and a feet massaging device disposed in a front inner portion of the main body for receiving the user's feet and massaging sole, top, and ankle of the feet.

Preferably, in the dry type half bath apparatus, the feet massaging device comprises: a receiving member provided at a front lower portion of the main body and comprising a tilted surface facing a rear top portion of the main body, wherein a pair of entrances are provided at the tilted surface so as to receive the user's feet; at least one acupressure roller provided on a bottom portion of the receiving member and configured for being operated by an electric motor and perform acupressure on the user's sole; and at least one airbag provided in the receiving member and configured for air's being blown in and out by a pump so as to perform acupressure foot top or ankle of the user.

More preferably, in the dry type half bath apparatus, the feet massaging device is configured for moving along a rail installed on a floor of the main body.

Also, the feet massaging device comprises a far-infrared lamp therein, performing a function of foot bath.

Here, a near-infrared lamp is installed in a bottom portion of the chair, performing a function of sitz bath.

Preferably, a rock salt is installed on the chair, which produces ions.

Preferably, the far-infrared generator comprises a first far-infrared lamp or heater installed on a front inner wall of the main body, a second far-infrared lamp or heater installed on a rear inner wall of the main body, a third far-infrared heater installed on a left and right side inner wall of the main body, and a fourth far-infrared heater installed on a floor of the main body.

More preferably, the second far-infrared lamp or heater is installed on a backrest of the chair, and wherein the backrest includes a 'S'-shaped surface configured for contacting and maintaining the user's back in the shape of 'S'.

Effects of Invention

According to the invention, feet massage can be done comfortably during half bath, and it is possible to massage entire portion of feet as well as the sole portion.

Also, according to the invention, sitz bath can be done during half bath through near-infrared lamp.

Also, according to the invention, the user can move the feet massaging device appropriately to the length of leg and perform feet massage.

DETAILED DESCRIPTION EMBODIMENTS OF THE INVENTION

Below, referring to the figures, the embodiments of a dry type half bath apparatus according to the invention are described in detail. By the way, in describing the invention, the terms standing for components of the invention have been named considering functions of each of the components, and therefore they should not be understood to limit the corresponding technological components of the invention.

Figure 1:
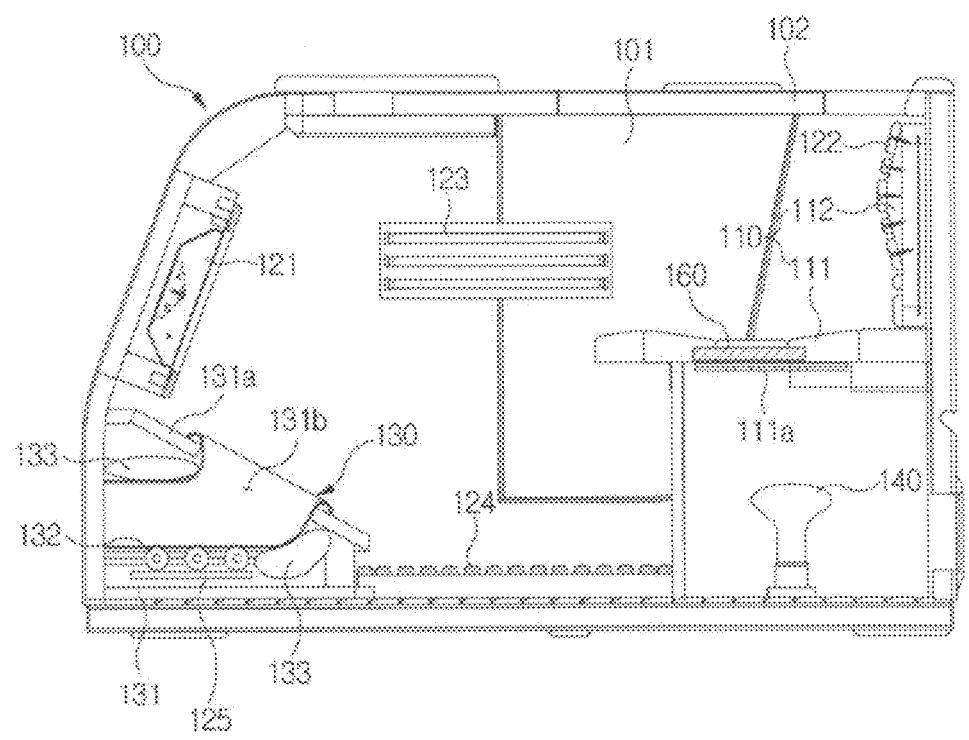
FIG. 1 is a side view showing a dry type half bath apparatus with feet massage function according to the invention.
Figure 2A:
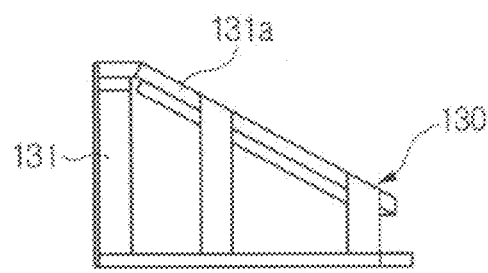
FIG. 2a is a side view showing a receiving member of a feet massaging device of FIG. 1.
Figure 2B:
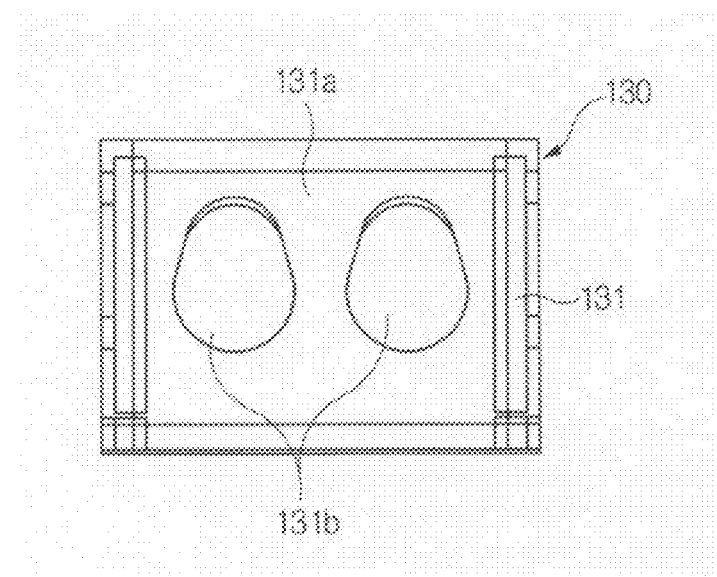
FIG. 2b is a front view showing a receiving member of a feet massaging device of FIG. 1.

Referring to FIGS. 1, 2a, and 2b, a dry type half bath apparatus with feet massage function includes a main body (100), a chair (110) provided in the main body (100), far-infrared generators (121, 122, 123, 124) disposed in the main body (100), and a feet massaging device (130) provided in the main body (100).

The main body (100) is a crate-shaped member having a specific space so as to receive the user's lower half body, and preferably made of red wood, spruce, hemlock spruce, etc. so as to minimize bending, splitting, knotting, gaping, etc. The main body (100) provides a door that opens and closes so as to allow the user to enter and go out. The door includes a side door (101) provided at a side surface of the main body (100) and a top door (102) provided on a top surface of the main body (100).

The chair (110) is installed in the rear inner portion of the main body (100) so as to enable the user to sit inside. The chair (110) includes a seat (111) for receiving the user's hip portion and a backrest (112) for supporting the user's back and waist.

The far-infrared generators (121, 122, 123, 124) are installed in the main body (100) and perform thermal action by illuminating far-infrared to the skin of the user sitting on the chair. The far-infrared from the far-infrared generators (121, 122, 123, 124) has wavelength above 25 μm, which penetrates deep into the skin causing thermal action. Such a thermal action helps to get rid of germs causing various diseases and to facilitate blood circulation and generation of cell tissue by expanding capillary blood vessels. Also, such a thermal action touches water and protein molecule and shakes them minutely by 2000 times a minute, facilitating the cellular organism so as to encourage prevention of aging, facilitation of metabolism, and prevention of adult diseases such as chronic fatigue.

Here, the far-infrared generators (121, 122, 123, 124) includes a first far-infrared lamp or heater (121), a second far-infrared lamp or heater (122), a third far-infrared heater (123), and a fourth far-infrared heater (124). The first far-infrared lamp or heater (121) is installed on a front inner wall of the main body and illuminates far-infrared toward the front of the user's lower half body. The second far-infrared lamp or heater (122) is installed on a rear inner wall of the main body (100) and illuminates far-infrared toward the user's back. The third far-infrared heater (123) is installed on left and right side inner wall of the main body (100) and illuminates far-infrared toward the side of the user's lower half body. The fourth far-infrared heater (124) is installed on a floor of the main body (100) and illuminates far-infrared evenly across the user's lower half body.

The feet massaging device (130, referring to FIGS. 2a and 2b) is provided in a front lower portion in the main body (100), and configured for receiving the feet of the user sitting on the chair (110) and massaging the entire feet of the user, that is, sole, top, and ankle of the feet.

In detail, the feet massaging device (130) includes a receiving member (131) provided in the front lower portion of the main body (100), an acupressure roller (132) installed in the receiving member (131), and an airbag (133).

The receiving member (131) is formed with a wooden material provided integrally with the main body (100) in a front lower edge portion of the main body (100). The receiving member (131) provides a tilted surface (131a) facing the rear top portion of the main body (100), and in the tilted surface (131a) are provided a pair of entrances (131b). Since the entrances (131b) are provided in the tilted surface (131a), the user can stretches feet while sitting on the chair (110) and put the feet in the receiving member (131) comfortably.

A plurality of acupressure rollers (132) separated by a specific interval are disposed on the floor of the receiving member (131), and operated by electrical motor (not shown), performing acupressure functions to the sole of the user.

The airbag (133) is put in or out with air by a pump (not shown), and can be disposed in the front, rear, and sides in the receiving member (131), so as to massaging top and ankle of feet.

As in the above, the dry type half bath apparatus with feet massaging function according to the invention enables feet massaging using the feet massaging device (130) during half bath, and the massaging can be done not only on the sole, but also over the entire feet.

Preferably, in the receiving member (131) of the feet massaging device may be installed a far-infrared lamp (125). The far-infrared lamp (125) may be installed on the floor of the receiving member (131) close to the acupressure roller (132). Here, the far-infrared lamp (125) illuminates far-infrared to the user's feet received in the receiving member (131), generating thermal effect and performing foot bath.

Therefore, the dry type half bath apparatus with feet massaging function according to the invention can perform the feet massaging function and the foot bath function during the half bath.

Preferably, the above second far-infrared lamp or heater (122) is installed in the backrest (112), and the backrest has an 'S'-shaped surface so as to contact the user's back and maintain the 'S' shape. By such backrest (112) and the second far-infrared lamp or heater (122), the user's posture is corrected so that the user's backbone is kept in the 'S' shape during the half bath, helping the backbone's health.

Again referring to FIG. 1, below the chair (110) is provided a near-infrared lamp (140) for illuminating near-infrared upward. And, in the center of the seat (111) of the chair (110) is formed a through-hole (111a), so that the near-infrared from the near-infrared lamp (140) is illuminated to the hip portion of the user sitting on the chair (110). Near-infrared from such near-infrared lamp (140) has a wavelength of 0.75~3 μm, which can be used for disinfection, sterilization, and curing of joint and muscle. Additionally, in the chair (110) can be installed a rock salt (160) in a planar shape.

Thus, the user can obtain the effects of sitz bath while enjoying half bath using the near-infrared lamp (140) installed below the chair (110).

Figure 3:
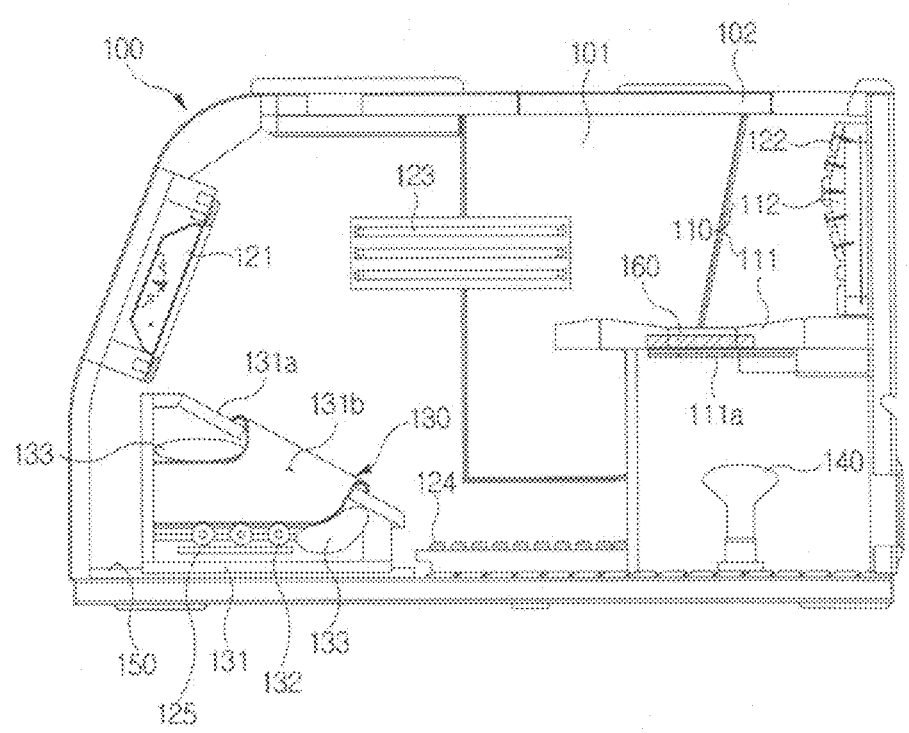
FIG. 3 is a side view showing another example of a dry type half bath apparatus with feet massage function according to the invention.

On the other hand, referring to FIG. 3, the dry type half bath apparatus with feet massaging function according to the invention is configured to be able to move the feet massaging device according to the length of lower half body of the user.

In detail, on the floor of the main body (100) is installed a rail (150) in a direction of length of the main body (100), and on the rail (150) is installed the receiving member (131) of the feet massaging device (130). The receiving member (131) can be moved forward or backward along the rail (150).

Therefore, the user can move the feet massaging device (130) to the length of his own legs, and then use it.

While the invention has been shown and described with reference to different embodiments thereof, it will be appreciated by those skilled in the art that variations in form, detail, compositions and operation may be made without departing from the spirit and scope of the invention as defined by the accompanying claims.

REFERENCE NUMERALS

100: main body 101, 102: door
110: chair 111: seat
111a: through-hole 112: backrest 121, 122, 123, 124, 125: far-infrared generator
130: feet massaging device
131: receiving member
131a: tilted surface 131b: entrance
132: acupressure roller 133: airbag
140: near-infrared lamp 150: rail
160: rock salt

What is claimed is:

1. A dry type half bath apparatus with feet massage function comprising:
   a main body comprising a door that opens and closes for a user's entering and leaving;
   a chair disposed in a rear inner portion of the main body for the user's sitting thereon;
   at least one far-infrared generater disposed in the main body and illuminating far-infrared to skin of the user sitting on the chair; and
   a feet massaging device disposed in a front inner portion of the main body for receiving the user's feet and massaging sole, top, and ankle of the feet.

2. The dry type half bath apparatus of claim 1, wherein the feet massaging device comprising:
   a receiving member provided at a front lower portion of the main body and comprising a tilted surface facing a rear top portion of the main body, wherein a pair of entrances are provided at the tilted surface so as to receive the user's feet;
   at least one acupressure roller provided on a bottom portion of the receiving member and configured for being operated by an electric motor and perform acupressure on the user's sole; and
   at least one airbag provided in the receiving member and configured for air's being blown in and out by a pump so as to perform acupressure foot top or ankle of the user.

3. The dry type half bath apparatus of claim 2, wherein the feet massaging device is configured for moving along a rail installed on a floor of the main body.

4. The dry type half bath apparatus of claim 3, wherein a near-infrared lamp is installed in a bottom portion of the chair, performing a function of sitz bath.

5. The dry type half bath apparatus of claim 4, wherein a rock salt is installed on the chair, which produces ions.

6. The dry type half bath apparatus of claim 3, wherein the far-infrared generator comprises a first far-infrared lamp or heater installed on a front inner wall of the main body, a second far-infrared lamp or heater installed on a rear inner wall of the main body, a third far-infrared heater installed on a left and right side inner wall of the main body, and a fourth far-infrared heater installed on a floor of the main body.

7. The dry type half bath apparatus of claim 6, wherein the second far-infrared lamp or heater is installed on a backrest of the chair, and wherein the backrest includes a 'S'-shaped surface configured for contacting and maintaining the user's back in the shape of 'S'.

8. The dry type half bath apparatus of claim 2, wherein the feet massaging device comprises a far-infrared lamp therein, performing a function of foot bath.

9. The dry type half bath apparatus of claim 8, wherein a near-infrared lamp is installed in a bottom portion of the chair, performing a function of sitz bath.

10. The dry type half bath apparatus of claim 9, wherein a rock salt is installed on the chair, which produces ions.

11. The dry type half bath apparatus of claim 8, wherein the far-infrared generator comprises a first far-infrared lamp or heater installed on a front inner wall of the main body, a second far-infrared lamp or heater installed on a rear inner wall of the main body, a third far-infrared heater installed on a left and right side inner wall of the main body, and a fourth far-infrared heater installed on a floor of the main body.

12. The dry type half bath apparatus of claim 11, wherein the second far-infrared lamp or heater is installed on a backrest of the chair, and wherein the backrest includes a 'S'-shaped surface configured for contacting and maintaining the user's back in the shape of 'S'.

13. The dry type half bath apparatus of claim 2, wherein a near-infrared lamp is installed in a bottom portion of the chair, performing a function of sitz bath.

14. The dry type half bath apparatus of claim 13, wherein a rock salt is installed on the chair, which produces ions.

15. The dry type half bath apparatus of claim 2, wherein the far-infrared generator comprises a first far-infrared lamp or heater installed on a front inner wall of the main body, a second far-infrared lamp or heater installed on a rear inner wall of the main body, a third far-infrared heater installed on a left and right side inner wall of the main body, and a fourth far-infrared heater installed on a floor of the main body.

16. The dry type half bath apparatus of claim 15, wherein the second far-infrared lamp or heater is installed on a backrest of the chair, and wherein the backrest includes a 'S'-shaped surface configured for contacting and maintaining the user's back in the shape of 'S'.

17. The dry type half bath apparatus of claim 1, wherein a near-infrared lamp is installed in a bottom portion of the chair, performing a function of sitz bath.

18. The dry type half bath apparatus of claim 17, wherein a rock salt is installed on the chair, which produces ions.

19. The dry type half bath apparatus of claim 1, wherein the far-infrared generator comprises a first far-infrared lamp or heater installed on a front inner wall of the main body, a second far-infrared lamp or heater installed on a rear inner wall of the main body, a third far-infrared heater installed on a left and right side inner wall of the main body, and a fourth far-infrared heater installed on a floor of the main body.

20. The dry type half bath apparatus of claim 19, wherein the second far-infrared lamp or heater is installed on a backrest of the chair, and wherein the backrest includes a 'S'-shaped surface configured for contacting and maintaining the user's back in the shape of 'S'.

* * * * *